US012279773B2

(12) United States Patent
Chang

(10) Patent No.: US 12,279,773 B2
(45) Date of Patent: Apr. 22, 2025

(54) SURGICAL STAPLING INSTRUMENT WITH CLAMP DETECTION ASSEMBLY

(71) Applicant: Covidien LP, Mansfield, MA (US)

(72) Inventor: Lan Chang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/294,672

(22) PCT Filed: Aug. 4, 2021

(86) PCT No.: PCT/CN2021/110437
§ 371 (c)(1),
(2) Date: Feb. 2, 2024

(87) PCT Pub. No.: WO2023/010304
PCT Pub. Date: Feb. 9, 2023

(65) Prior Publication Data
US 2024/0341760 A1    Oct. 17, 2024

(51) Int. Cl.
*A61B 17/072*    (2006.01)
*A61B 90/00*    (2016.01)
*A61B 17/00*    (2006.01)

(52) U.S. Cl.
CPC ........ *A61B 17/07207* (2013.01); *A61B 90/08* (2016.02); *A61B 2017/00017* (2013.01);
(Continued)

(58) Field of Classification Search
CPC .............................................. A61B 17/07207
See application file for complete search history.

(56) References Cited

U.S. PATENT DOCUMENTS 5,074,454 A * 12/1991 Peters .............. A61B 17/07207
227/19
5,988,479 A    11/1999 Palmer
8,453,907 B2 * 6/2013 Laurent .................. A61B 90/30
227/176.1

FOREIGN PATENT DOCUMENTS

CN    202568353 U    12/2012
CN    103037780 A    4/2013
(Continued)

OTHER PUBLICATIONS

International Search Report dated Apr. 26, 2022, issued in corresponding international appln No. PCT/CN2021/110437, 3 pages.
(Continued)

*Primary Examiner* — Nathaniel C Chukwurah

(57) ABSTRACT

A surgical stapling instrument (10) includes anvil and cartridge portions (100, 200) operably coupled together. The anvil and cartridge portions (100, 200) are transitionable between clamped and unclamped configurations. The surgical stapling instrument (10) also includes a clamp detection assembly (300) with a plunger (312) slidably disposed in a chamber (310) of a housing (302), a block (314) with an aperture (316) attached to the plunger (312), a spring (318) disposed in the chamber (310), and a button (340) slidably disposed in a recess (180) of the anvil portion (100). The spring (318) biases the plunger (312) and block (314) towards the cartridge portion (200) such that the aperture (316) is out of alignment with the button (340) in the unclamped configuration and engagement of the plunger (312) with a bridge (254) of the cartridge portion (200) translates the plunger (312) and the block (314) away from the opening of the chamber (310) such that the aperture (316) is aligned with the button (340) in the clamped configuration.

20 Claims, 12 Drawing Sheets

(52) U.S. Cl.
CPC .............. *A61B 2017/00398* (2013.01); *A61B 2017/00477* (2013.01); *A61B 2017/00734* (2013.01); *A61B 2017/07257* (2013.01); *A61B 2017/07271* (2013.01); *A61B 2090/0807* (2016.02)

(56) References Cited

FOREIGN PATENT DOCUMENTS

| | | |
|---|---|---|
| CN | 105682569 A | 6/2016 |
| CN | 112584778 A | 3/2021 |
| CN | 112822986 A | 5/2021 |
| EP | 3 066 993 A1 | 9/2016 |
| EP | 3 469 995 A1 | 4/2019 |

OTHER PUBLICATIONS

Partial Supplementary European Search Report for European Patent Application No. 21952213.3 mailed Mar. 3, 2025, 13 pages.

* cited by examiner

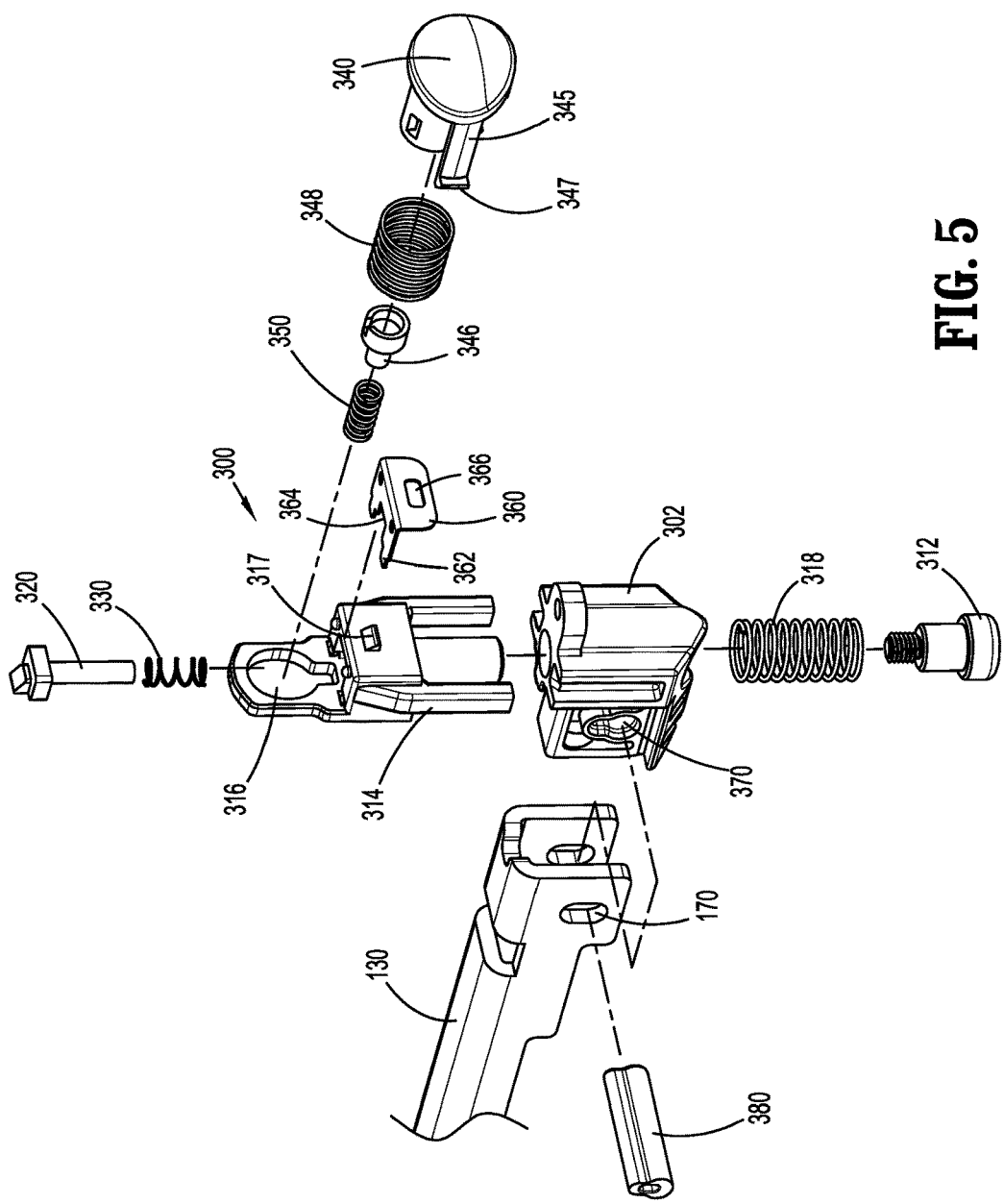
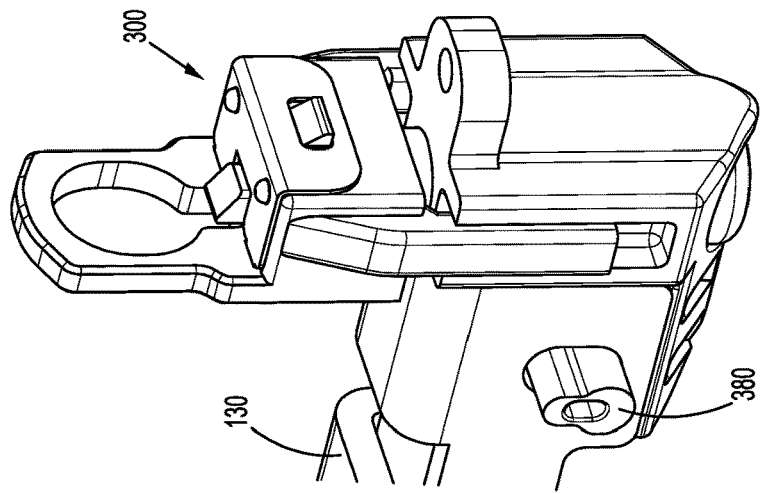
FIG. 5
FIG. 4

SURGICAL STAPLING INSTRUMENT WITH CLAMP DETECTION ASSEMBLY

FIELD

The present disclosure generally relates to surgical stapling instruments. In particular, the present disclosure relates to a surgical stapling instrument with a clamp detection assembly.

BACKGROUND

Surgical stapling instruments are employed by surgeons to sequentially or simultaneously apply one or more rows of fasteners, e.g., staples or two-part fasteners, to body tissue for the purpose of joining segments of body tissue together. Such apparatus generally includes a pair of jaws or finger-like structures between which the body tissue to be joined is placed. When the surgical stapling instrument is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the instrument to cut the body tissue between the lines of staples.

Surgical stapling instruments for performing anastomoses are well known in the art, and typically include an anvil assembly that is movable relative to a cartridge assembly to compress, and subsequently, staple tissue therebetween. The tissue is compressed as the anvil assembly is pivoted relative to the cartridge assembly to create a clamping action. Once a tissue gap, e.g., a distance between the anvil assembly and the cartridge assembly, achieves a predetermined range, the surgical stapling instrument may be fired.

SUMMARY

In accordance with an aspect of the present disclosure, a surgical stapling instrument includes an anvil portion and a cartridge portion operably coupled thereto. The anvil and cartridge portions are transitionable between clamped and unclamped configurations. The surgical stapling instrument also includes a clamp detection assembly with a plunger slidably disposed in a chamber of a housing. A block is attached to the plunger and has an aperture. A spring is disposed in the chamber and biases the plunger and block towards the cartridge portion. A button is slidably disposed in a recess of the anvil portion and includes a distal face and a projection. The spring urges the plunger and the block towards an opening of the chamber such that the aperture is out of alignment with the button in the unclamped configuration of the anvil and cartridge portions. Engagement of the plunger with a bridge of the cartridge portion translates the plunger and block away from the opening of the chamber such that the aperture is aligned with the button in the clamped configuration of the anvil and cartridge portions.

In aspects of the present disclosure, the surgical stapling instrument may further include a firing assembly having an actuation knob translatable along a length of the cartridge portion, a lead screw, and a slider coupled to the lead screw such that rotation of the lead screw causes axial displacement of the slider. The slider may be configured to detachably engage the actuation knob to impart axial displacement to the actuation knob.

In one aspect of the present disclosure, the surgical stapling instrument may further include an actuation assembly with a motor operatively coupled to the lead screw, a battery pack electrically coupled to the motor to supply power thereto, and a first switch electrically coupled to the motor.

In an aspect of the present disclosure, the distal face and the projection of the button may be translatable through the aperture with the anvil and cartridge portions in the clamped configuration.

In a further aspect of the present disclosure, the projection may be configured to engage a second switch of the actuation assembly and the second switch may enable activation of the motor.

In another aspect of the present disclosure, the first switch may be transitionable between a first position that rotates the motor in a first direction causing rotation of the lead screw in the first direction and a second position that rotates the motor in a second, and opposite, direction causing rotation of the lead screw in the second direction.

In aspects of the present disclosure, the battery pack may be replaceable.

In yet another aspect of the present disclosure, the slider may engage the actuation knob with the anvil and cartridge portions in the clamped configuration.

In accordance with another aspect of the present disclosure, a surgical stapling instrument has a cartridge portion configured to receive a loading unit and an anvil portion operably coupled to the cartridge portion. The anvil and cartridge portions are transitionable between clamped and unclamped configurations. The surgical stapling instrument also includes a firing assembly with an actuation knob translatable along a length of the cartridge portion, a lead screw, and a slider coupled to the lead screw such that rotation of the lead screw causes axial displacement of the slider. The slider is configured to detachably engage the actuation knob to impart axial displacement to the actuation knob. The surgical stapling instrument also includes an actuation assembly having a motor operatively coupled to the lead screw, a battery pack electrically coupled to the motor to supply power thereto, and a first switch electrically coupled to the motor. The first switch is transitionable between a first position that rotates the motor in a first direction causing rotation of the lead screw in the first direction and a second position that rotates the motor in a second, and opposite, direction causing rotation of the lead screw in the second direction. Actuation of a second switch on the anvil portion enables activation of the motor. The second switch is actuatable when the anvil and cartridge portions are in the clamped configuration.

In an aspect of the present disclosure, the surgical stapling instrument may include a button that is slidably disposed in a recess of the anvil portion and engageable with the second switch with the anvil and cartridge portions in the clamped configuration.

In aspects of the present disclosure, the surgical stapling instrument may also include a block with an aperture that is slidably disposed in the anvil portion. The aperture may be out of alignment with the button in the unclamped configuration of the anvil and cartridge portions and the aperture may be aligned with the button in the clamped configuration of the anvil and cartridge portions.

In one aspect of the present disclosure, the surgical stapling instrument may also include a plunger attached to the block and slidably disposed in the chamber of a housing and a spring biasing the plunger towards the cartridge portion. The spring may urge the plunger and block towards the cartridge portion such that the aperture is out of alignment with the button in the unclamped configuration of the anvil and cartridge portions. Engagement of the plunger with a bridge of the cartridge portion may translate the block towards the anvil portion such that the aperture is aligned with the button in the clamped configuration of the anvil and cartridge portions.

In aspects of the present disclosure, the battery pack may be replaceable.

In a further aspect of the present disclosure, the slider may engage the actuation knob with the anvil and cartridge portions in the clamped configuration.

According to an aspect of the present disclosure, a surgical stapling instrument has an anvil portion and a cartridge portion operably coupled thereto. The anvil and cartridge portions are transitionable between clamped and unclamped configurations. The surgical stapling instrument also includes a button slidably disposed in a recess of the anvil portion and a block with an aperture that is slidably disposed in the anvil portion. The aperture is out of alignment with the button in the unclamped configuration of the anvil and cartridge portions and the aperture is aligned with the button in the clamped configuration of the anvil and cartridge portions. An actuation knob is translatable along a length of the cartridge portion. The surgical stapling instrument includes a lead screw and a slider coupled to the lead screw such that rotation of the lead screw causes axial displacement of the slider, the slider engaging the actuation knob to impart axial displacement to the actuation knob with the anvil and cartridge portions in the clamped configuration.

In aspects of the present disclosure, the surgical stapling instrument may also include a motor operatively coupled to the lead screw, a battery pack electrically coupled to the motor to supply power thereto, and a first switch electrically coupled to the motor and configured to select a direction of rotation of the motor. The button may contact a second switch on the anvil portion and enable activation of the motor with the anvil and cartridge portions in the clamped configuration.

In a further aspect of the present disclosure, the battery pack is replaceable.

In yet a further aspect of the present disclosure, the surgical stapling instrument may further include a plunger attached to the block and slidably disposed in a chamber of a housing and a spring biasing the plunger towards the cartridge portion. The spring may urge the plunger and block towards the cartridge portion such that the aperture is out of alignment with the button in the unclamped configuration of the anvil and cartridge portions and engagement of the plunger with a bridge of the cartridge portion may translate the block towards the anvil portion such that the aperture is aligned with the button in the clamped configuration of the anvil and cartridge portions.

In another aspect of the present disclosure, the slider may be disengaged from the actuation knob with the anvil and cartridge portions in the unclamped configuration.

In yet another aspect of the present disclosure, the first switch may be transitionable between a first position that rotates the motor in a first direction causing rotation of the lead screw in the first direction and a second position that rotates the motor in a second, and opposite, direction causing rotation of the lead screw in the second direction.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 4 is an enlarged view of the indicated area of detail shown in FIG. 3 illustrating a safety button assembly;

FIG. 5 is an exploded perspective view, with parts separated, of the safety button assembly of FIG. 4;

DETAILED DESCRIPTION

Figure 1:
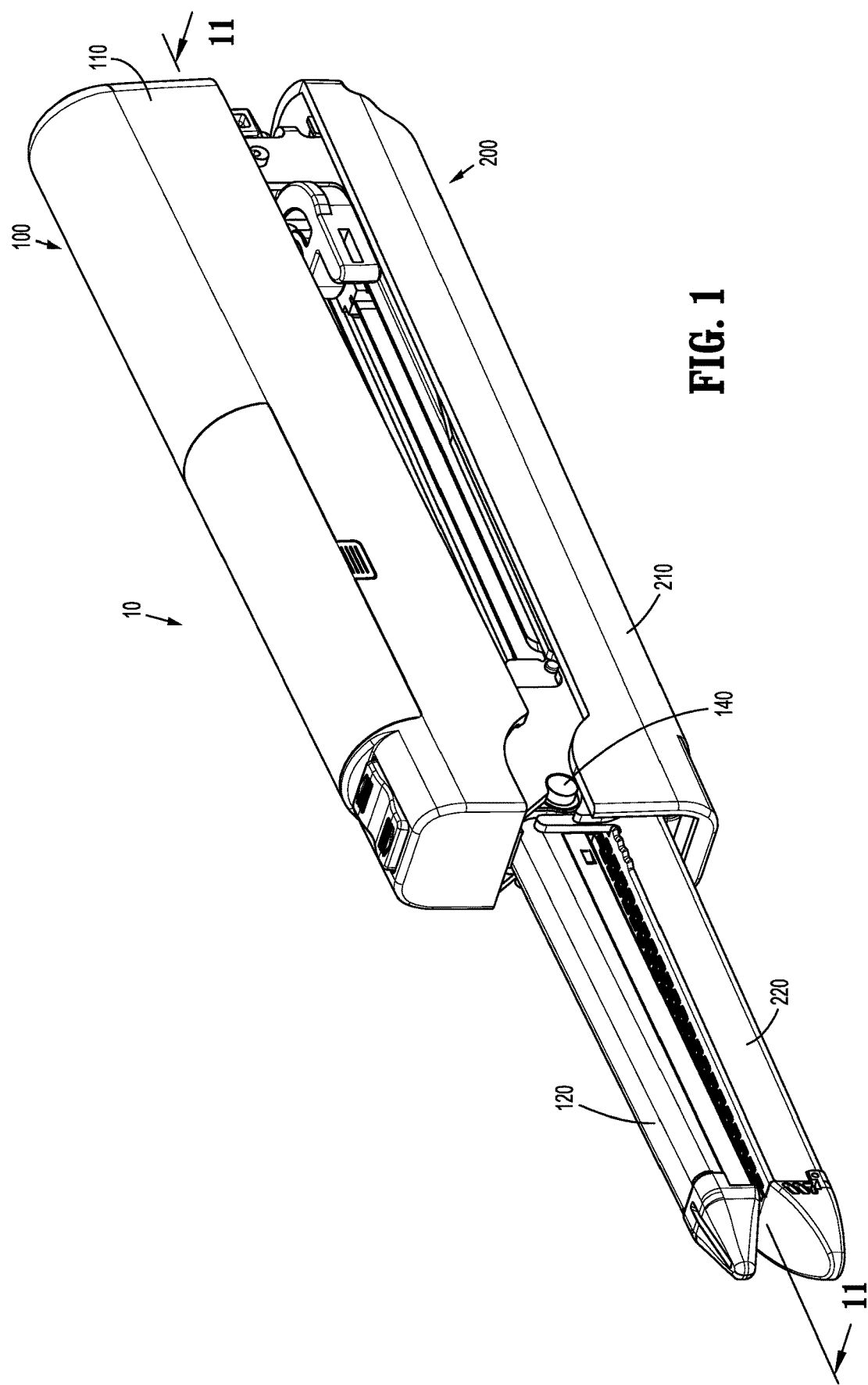
FIG. 1 is a perspective view of a surgical stapling instrument according to an aspect of the present disclosure.

The disclosed surgical stapling instrument will now be described in more detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as horizontal, vertical, distal, proximal, and similar terms are used to assist in understanding the description and are not intended to limit the disclosure.

As used herein, the term "distal" refers to the portion of the stapling device that is being described which is further from a user, while the term "proximal" refers to the portion of the stapling device that is being described which is closer to a user. Further, to the extent consistent, any of the aspects and features detailed herein may be used in conjunction with any or all the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system).

Descriptions of technical features or aspects of the disclosure should typically be considered as available and applicable to other similar features or aspects of the disclosure. Accordingly, technical features described herein according to one exemplary aspect of the disclosure may be applicable to other exemplary aspects of the disclosure, and thus duplicative descriptions may be omitted herein.

Figure 2:
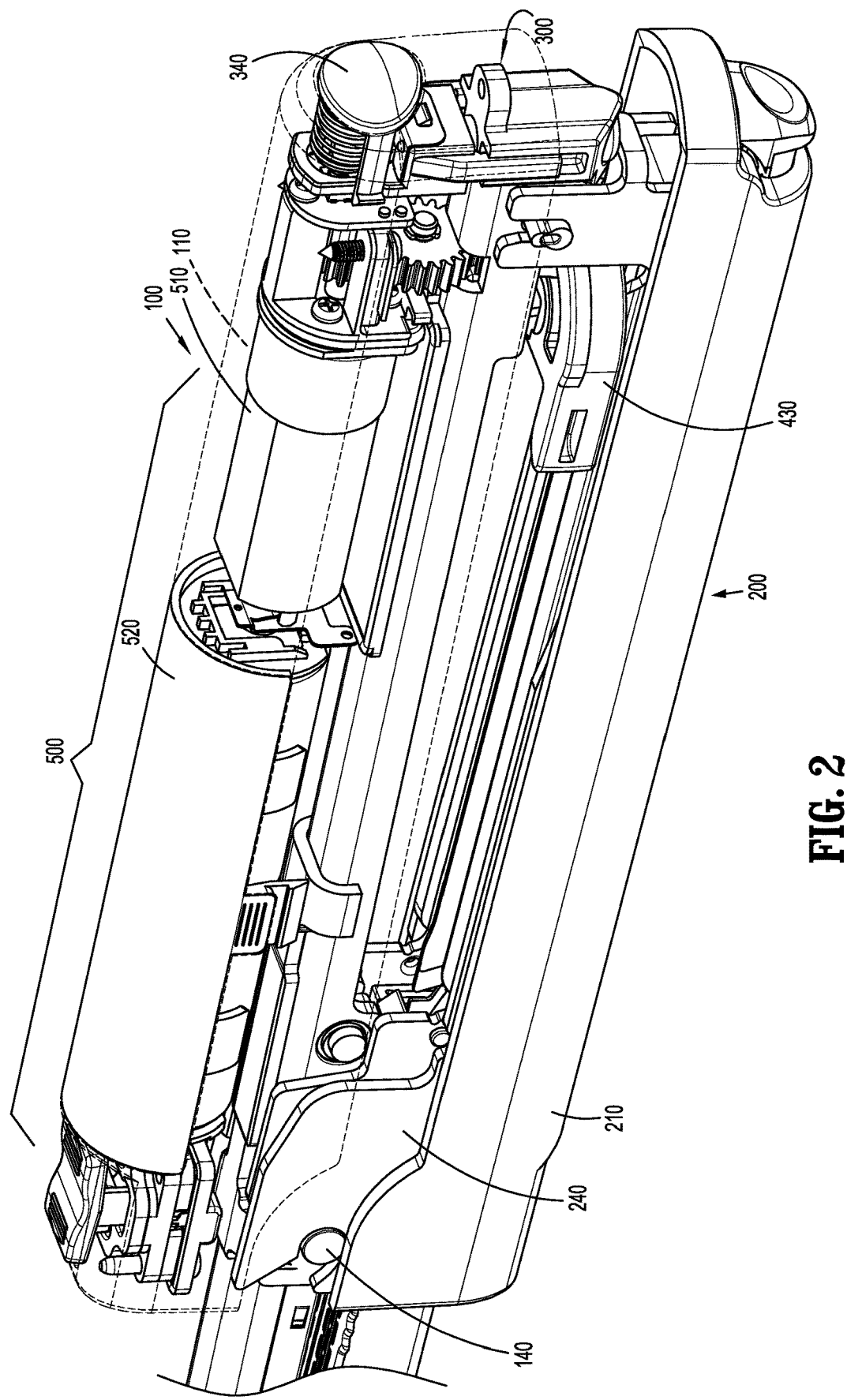
FIG. 2 is a perspective view of a handle assembly of the surgical stapling instrument of FIG. 1 with an anvil cover shown in phantom.
Figure 3:
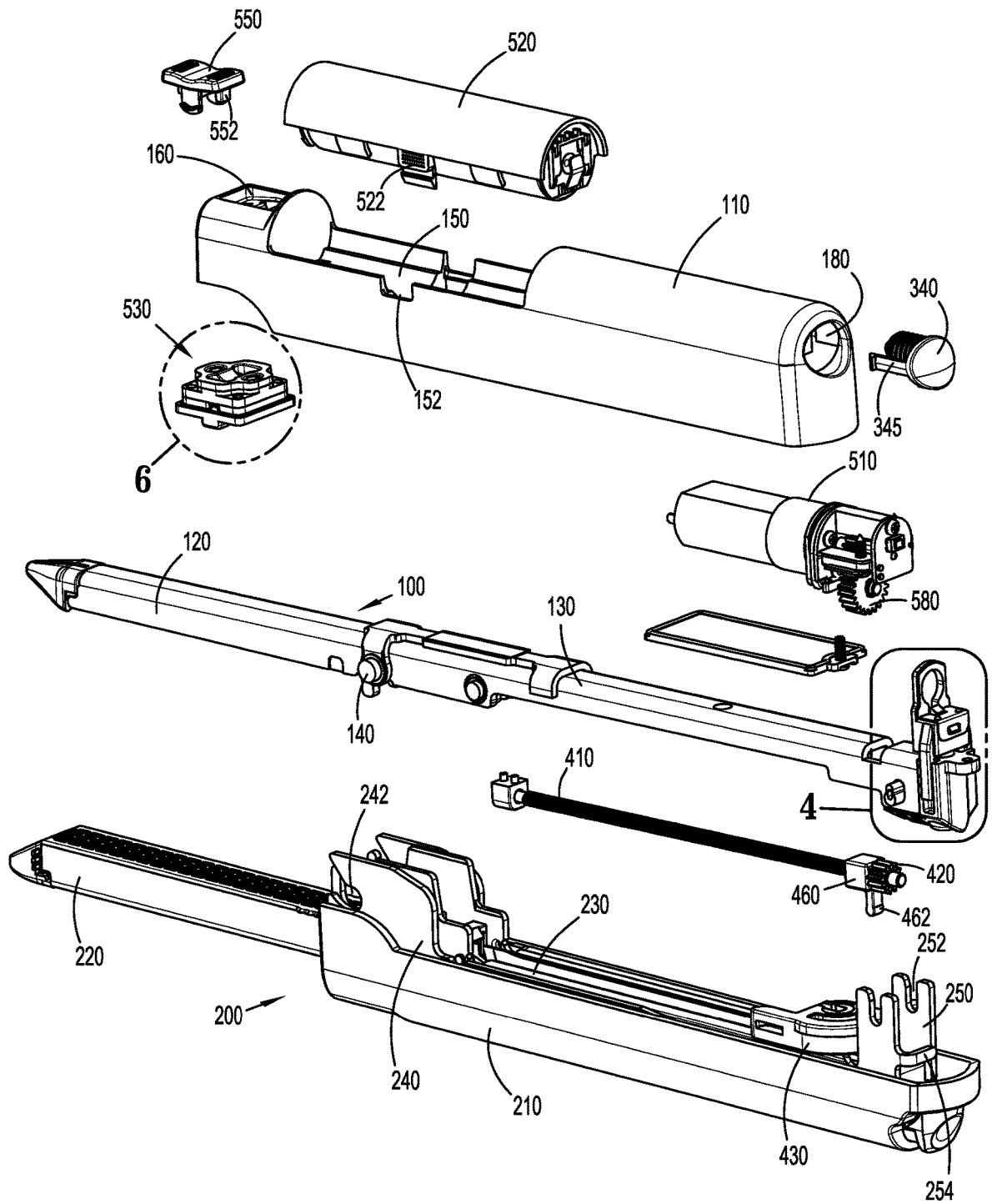
FIG. 3 is an exploded perspective view, with parts separated, of the surgical stapling instrument of FIG. 1.

Initially, with reference to FIGS. 1-3, a surgical stapling instrument according to the present disclosure is shown as surgical stapling instrument 10. The surgical stapling instrument 10 includes an anvil portion 100 pivotably and releasably coupled to a cartridge portion 200. The anvil portion 100 includes an anvil or first jaw 120 extending from an anvil body 130. The anvil portion 100 extends along a longitudinal axis "X-X" (FIG. 11) of the surgical stapling instrument 10. Opposing studs 140 extend from a proximal region of the first jaw 120 and are perpendicular to the longitudinal axis "X-X". The studs 140 are located in a region that separates the first jaw 120 from the anvil body 130. A proximal region of the anvil body 130 is configured to receive a clamp detection assembly 300 (FIG. 5) as will be explained in detail hereinafter. An anvil or first handle cover 110 is attached to the anvil body 130 and supports an actuation assembly 500. The actuation assembly 500 has a motor 510 electrically coupled to a battery pack 520. The battery pack 520 is releasably received in a cavity 150 of the first handle cover 110. The battery pack 520 includes opposed tabs 522 that engage notches 152 of the cavity 150 to releasably retain the battery pack 520 in the cavity 150 of the first handle cover 110. The battery pack 520 is removable from the first handle cover 110 allowing a depleted battery pack 520 to be replaced during a procedure. The battery pack 520 may be rechargeable or may have disposable batteries. A recess 160 that is configured to receive a first or actuation switch 530 that is part of the actuation assembly 500 is located distally of the cavity 150. Details of the actuation switch 530 will be discussed hereinafter. An opening 180 is positioned at a proximal end of the first handle cover 110 and is configured to receive a button or safety button 340 therein. The button 340 is part of the clamp detection assembly 300. The motor 510 is positioned in a proximal region of the first handle cover 110 and is electrically coupled to the battery pack 520. The battery pack 520 supplies electrical power to the motor 510 using contacts on the motor 510 and battery pack 520 as is known in the art. A drive gear 570 is rotatably coupled to the motor 510 such that when the motor 510 rotates in a first direction, the drive gear 570 also rotates in the first direction. Similarly, when the motor 510 rotates in a second direction, the drive gear 570 also rotates in the second direction. The drive gear 570 engages an intermediate gear 580 (FIG. 15) for imparting rotational motion to a gear 420 of a lead screw 410 as will be explained hereinafter. At the proximal end of the motor 510, a second or safety switch 560 is positioned on a wall of the motor 510. The safety switch 560 is transitionable between a first or disengaged position and a second or engaged position. As will be discussed in further detail hereinbelow, the safety switch 560 is transitioned from the disengaged position to the engaged position by its interaction with the safety button 340. In the disengaged position, electrical power to the motor 510 is interrupted thereby preventing the motor 510 from operating. In the engaged position, electrical power may be transmitted to the motor 510 such that the motor 510 is operable. Essentially, the safety switch 560 acts as an interlock preventing operation of the motor 510 when the safety button 340 is not actuated (i.e., depressed).

The cartridge portion 200 has a second jaw 220 that is configured to receive a cartridge with surgical fasteners (not shown) therein. A suitable cartridge including surgical fasteners is disclosed in commonly owned U.S. Pat. Nos. 7,721,933 and 8,505,801, the entire contents of which are hereby incorporated by reference. The cartridge portion 200 includes the second jaw 220 extending from a cartridge body 230. A support 240 is located at a proximal end of the second jaw 220 and has receptacles 242 configured to receive the studs 140 of the anvil portion 100. The receptacles 242 are open and face the distal end of the second jaw 220 member. With the studs 140 of the anvil portion 100 disposed in the receptacles 242 of the support 240, the anvil portion 100 is releasably and pivotably coupled to the cartridge portion 200. As such, the anvil and cartridge portions 100, 200 are transitionable between a clamped configuration where the first and second jaws 120, 220 are in close cooperative alignment (see FIG. 1) and an unclamped configuration where the first and second jaws 120, 220 are spaced apart defining an acute angle therebetween (see FIG. 8). This also defines the clamped and unclamped configurations of the surgical stapling instrument 10. In the unclamped configuration, the first and second jaws 120, 220 are spaced apart such that the surgical stapling instrument 10 can receive body tissue between the first and second jaws 120, 220. In the clamped configuration, body tissue that is positioned between the first and second jaws 120, 220 is secured therebetween. A cartridge or second handle cover 210 is attached to the cartridge body 230 and supports a firing assembly 400. The firing assembly 400 has the lead screw 410 extending along the cartridge body 230. The lead screw 410 has helical threads thereon and rotatably supports a slider 460 thereon. The gear 420 is located at a proximal end of the lead screw 410 and is configured to engage the intermediate gear 580 that is rotatably coupled to the drive gear 570 of the motor 510. When the drive gear 570 of the motor 510 is coupled with the gear 420 of the lead screw 410, rotation of the motor 510 causes rotation of the lead screw 410. The lead screw 410 is rotatable about the longitudinal axis "X-X" while remaining longitudinally stationary. The slider 460 has a finger 462 extending therefrom which is configured to releasably engage a cutout 432 of an actuation knob 430. With additional reference to FIG. 11, a drive bar 440 extends distally from the actuation knob 430. The drive bar 440 is coupled to a sled 450 with a knife 452 such that distal translation of the drive bar 440 and sled 450 is configured to sequentially eject surgical fasteners from the cartridge as indicated by arrows "F" in FIG. 15. Rotating the lead screw 410 in a first direction causes translation of the slider 460 towards a distal end of the cartridge body 230 and rotating the lead screw 410 in a second direction that is opposite the first direction causes translation of the slider 460 towards a proximal end of the cartridge body 230. When the finger 462 of the slider 460 is positioned in the cutout 432 of the actuation knob 430 (FIG. 12), rotational movement of the lead screw 410 is communicated to the actuation knob 430 such that movement of the slider 460 along the longitudinal axis "X-X" in either direction causes concomitant longitudinal movement of the actuation knob 430, the drive bar 440, and the sled 450.

Figure 10:
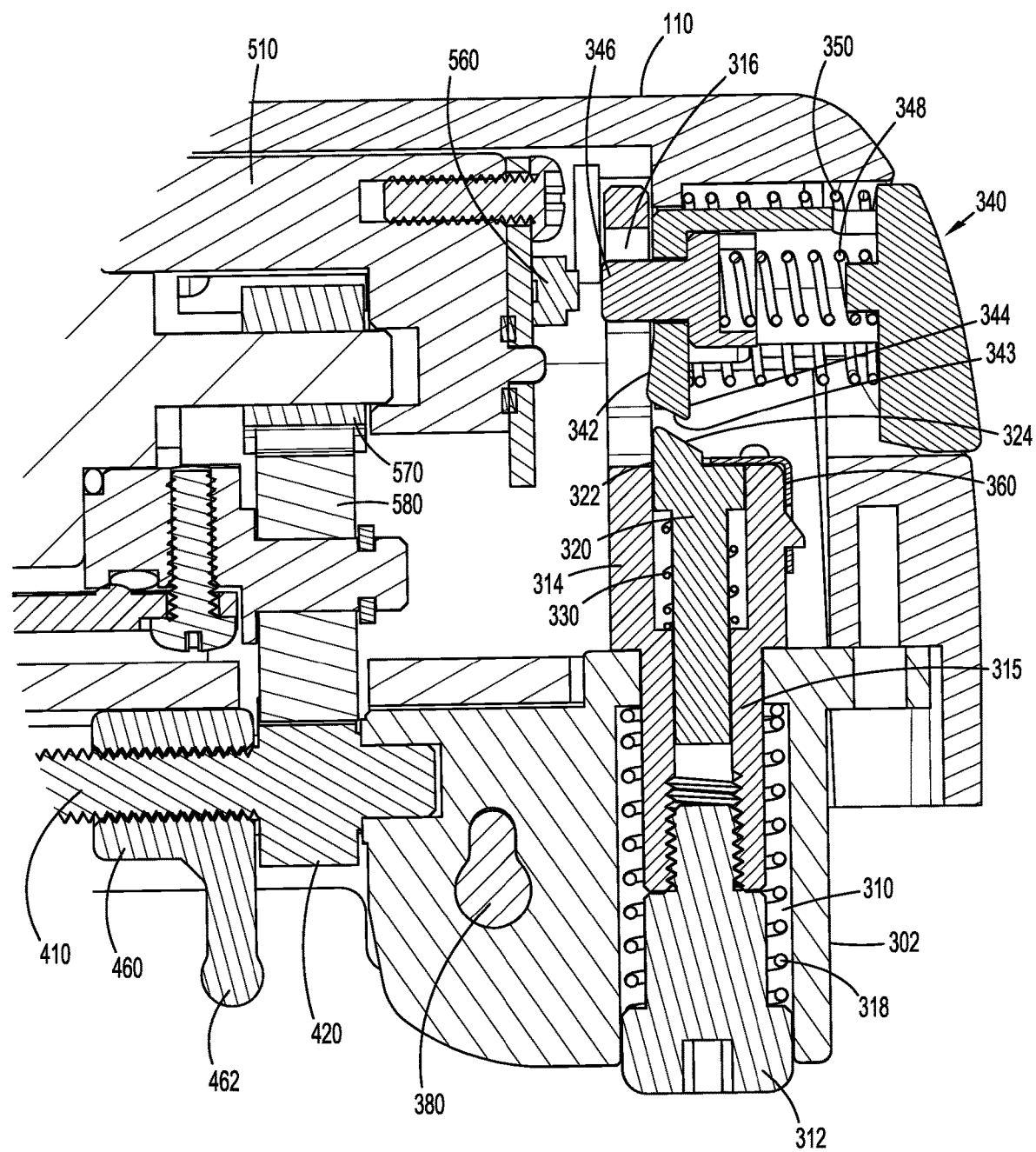
FIG. 10 is an enlarged view of the indicated area of detail shown in FIG. 9 illustrating a clamp detection assembly with the surgical stapling instrument in an unclamped configuration.

With reference now to FIGS. 4, 5, and 10, details of the clamp detection assembly 300 are illustrated. The clamp detection assembly 300 is attached to a proximal end of the anvil body 130. The proximal end of the anvil body 130 has a U-shaped configuration that is adapted for receiving a housing 302 of the clamp detection assembly 300 therein. Opposing sidewalls of the anvil body 130 have oblong openings 170 for slidably receiving a rod 380 therethrough. The housing 302 has a passage 370 with a keyhole configuration that allows insertion of the rod 380 in a specific orientation. With the housing 302 positioned in anvil body 130, the rod 380 is insertable through the openings 170 of the sidewalls of the anvil body 130 and the passage 370 of the housing 302, thereby attaching the housing 302 to the anvil body 130. The housing 302 has a chamber 310 with opposed top and bottom openings and is configured to receive a plunger or pusher 312 and a first spring 318 therein. The first spring 318 has an inner diameter that accommodates a body of the plunger 312 and one end of the first spring 318 rests against a shoulder of the plunger 312. An opposed end of the first spring 318 rests against a wall of the chamber 310 and the first spring 318 biases the plunger 312 towards the bottom opening of the chamber 310 and towards the cartridge body 230. A safety block or block 314 has a column 315 that is insertable into the top opening of the chamber 310. Additionally, the column 315 has internal threads that mate with external threads of the plunger 312 thereby coupling them together. A shoulder of the block 314 rests on an upper surface of the housing 302. The shoulder of the block limits travel of the plunger 312 that is attached thereto. Extending from one side of the block 314 is a wall with an aperture 316 therethrough. The aperture 316 is configured to allow passage of a distal face 342 of the safety button 340 therethrough. As assembled, the first spring 318 biases the plunger 312 and the block 314 towards the cartridge body 230 and engagement of the shoulder of the block 314 with the upper surface of the housing 302 limits travel of the plunger 312 such that the plunger 312 is retained in the chamber 302.

The block 314 also has a cavity that receives a safety pin 320 and a second or safety spring 330. The safety pin 320 has a head with a planar distal face 322 that slidably engages an inner surface of the wall of the block 314. The safety pin 320 is biased towards the first handle cover 110 by the second spring 330. Further, the head of the safety pin 320 has an angled face 324 that is configured to engage an angled surface 343 of the safety button 340 as will be explained hereinafter. The safety pin 320 is retained in the cavity by a retainer plate 360 that is attached to the block 314 and limits the travel of the safety pin 320 towards the first handle cover 110. In particular, the retainer plate 360 has a hole 366 that receives a tab 317 of the block 314 therethrough and legs 362 separated by a notch 364 that straddle the angled face 324 of the safety pin 320. The safety button 340 is disposed in a recess 180 of the first handle cover 110. The safety button 340 has legs 345 extending distally into the recess 180 and each leg 345 includes a tab 347 for engaging an inner surface of the recess 180 to retain the safety button 340 therein. The safety button 340 also includes a body with a distal face 342 and a projection 346 extending from the distal face 342. The angled surface 343 of the safety button 340 extends from the distal face 342. The angled surface has a complementary angle to the angled face 324 of the head of the safety pin 320. A third spring 348 is positioned in a hollow of the body of the safety button 340. One end of the third spring 348 rests against an inner surface of the projection 346 and the other end of the third spring 348 abuts an inner surface of the safety button 340 thereby biasing the projection 346 distally. A fourth spring 350 surrounds the body of the safety button 340 and biases the safety button 340 proximally in the first handle cover 110 such that a portion of the safety button 340 is readily accessible by a user. As is evident in FIG. 10, a distal portion of the projection 346 is aligned with a second or safety switch 560 of the actuation assembly 500.

Figure 6:
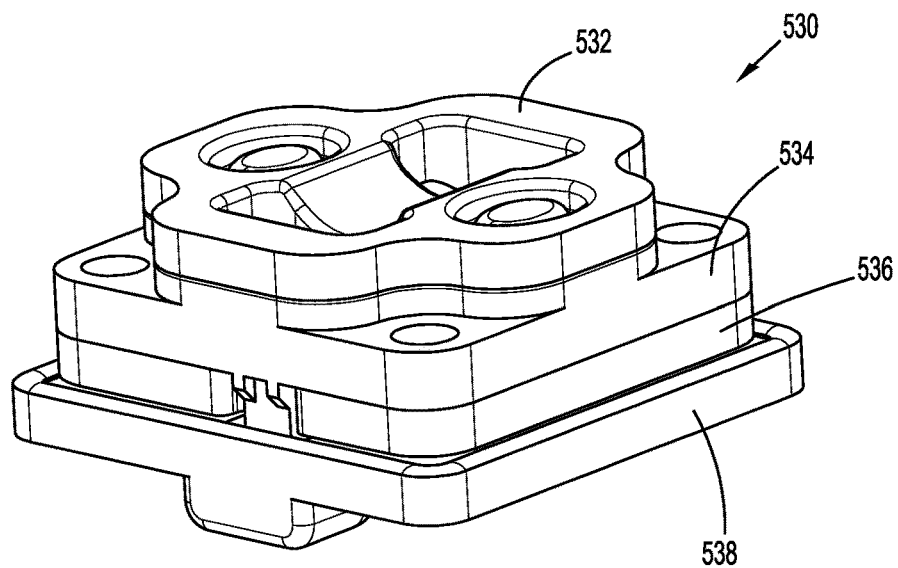
FIG. 6 is an enlarged view of the indicated area of detail shown in FIG. 3 illustrating an actuation button assembly.
Figure 7:
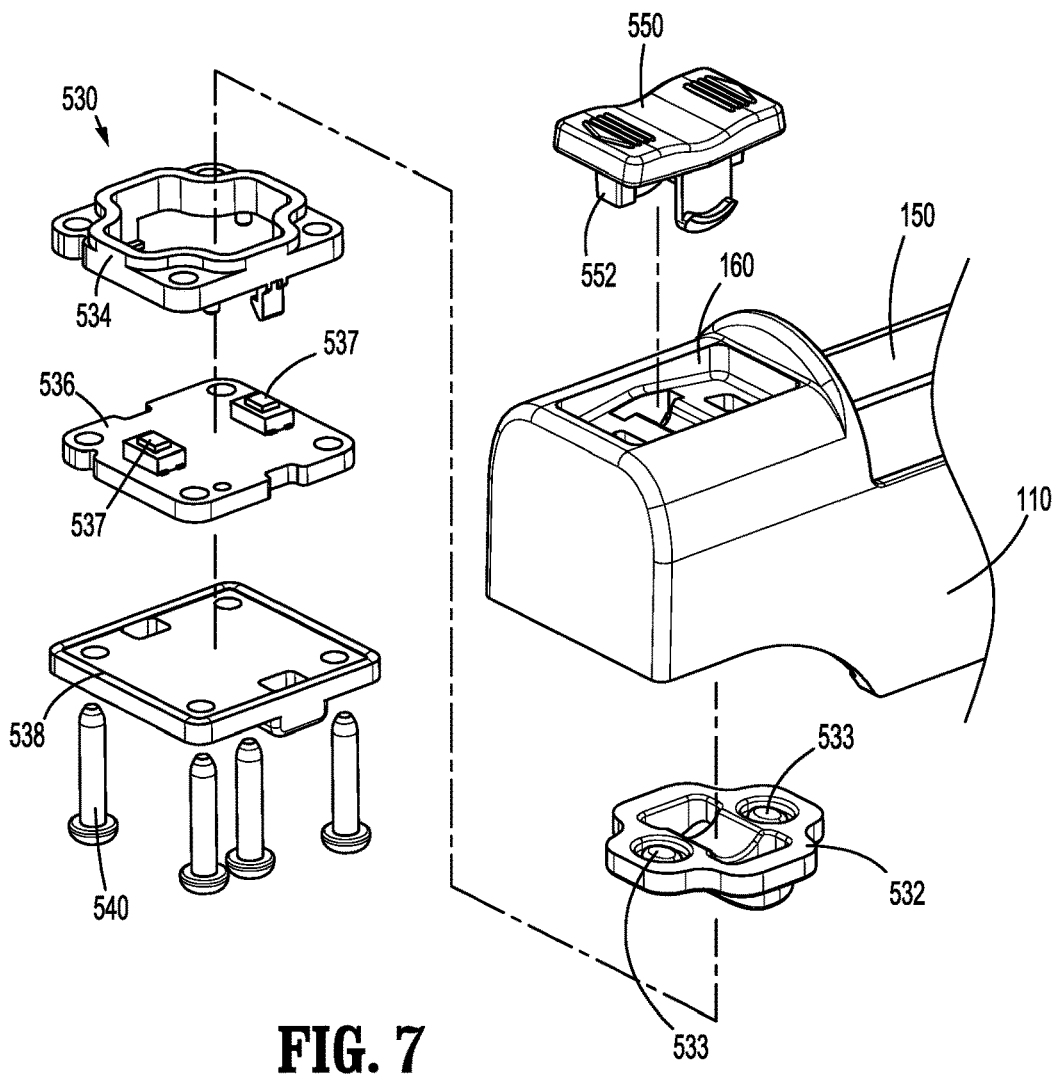
FIG. 7 is an exploded perspective view, with parts separated, illustrating attachment of the actuation button assembly to the anvil cover.
Figure 9:
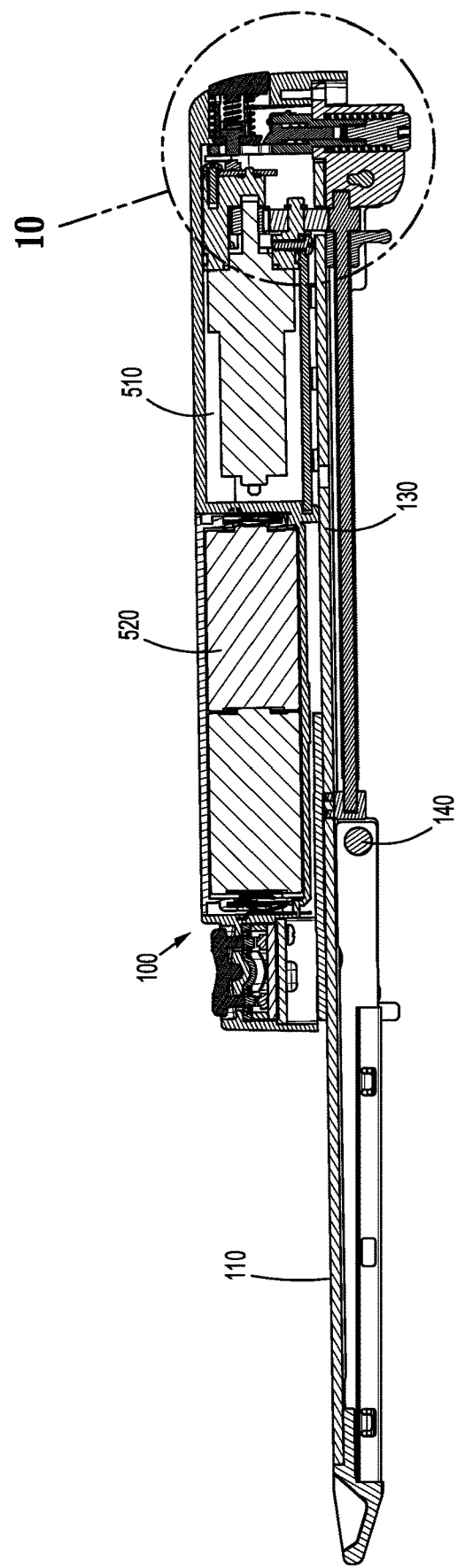
FIG. 9 is a side cross-sectional view taken along section line 9-9 of FIG. 8.
Figure 11:
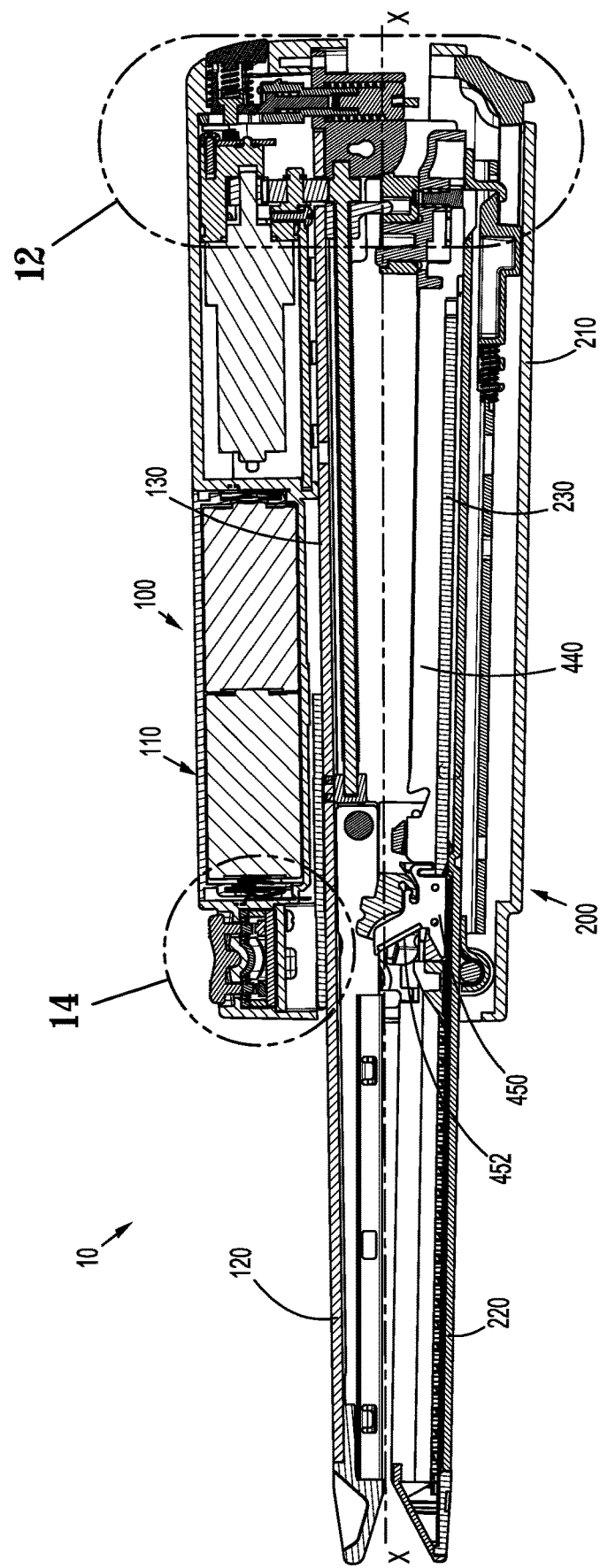
FIG. 11 is a side cross-sectional view taken along section line 11-11 of FIG. 1.
Figure 12:
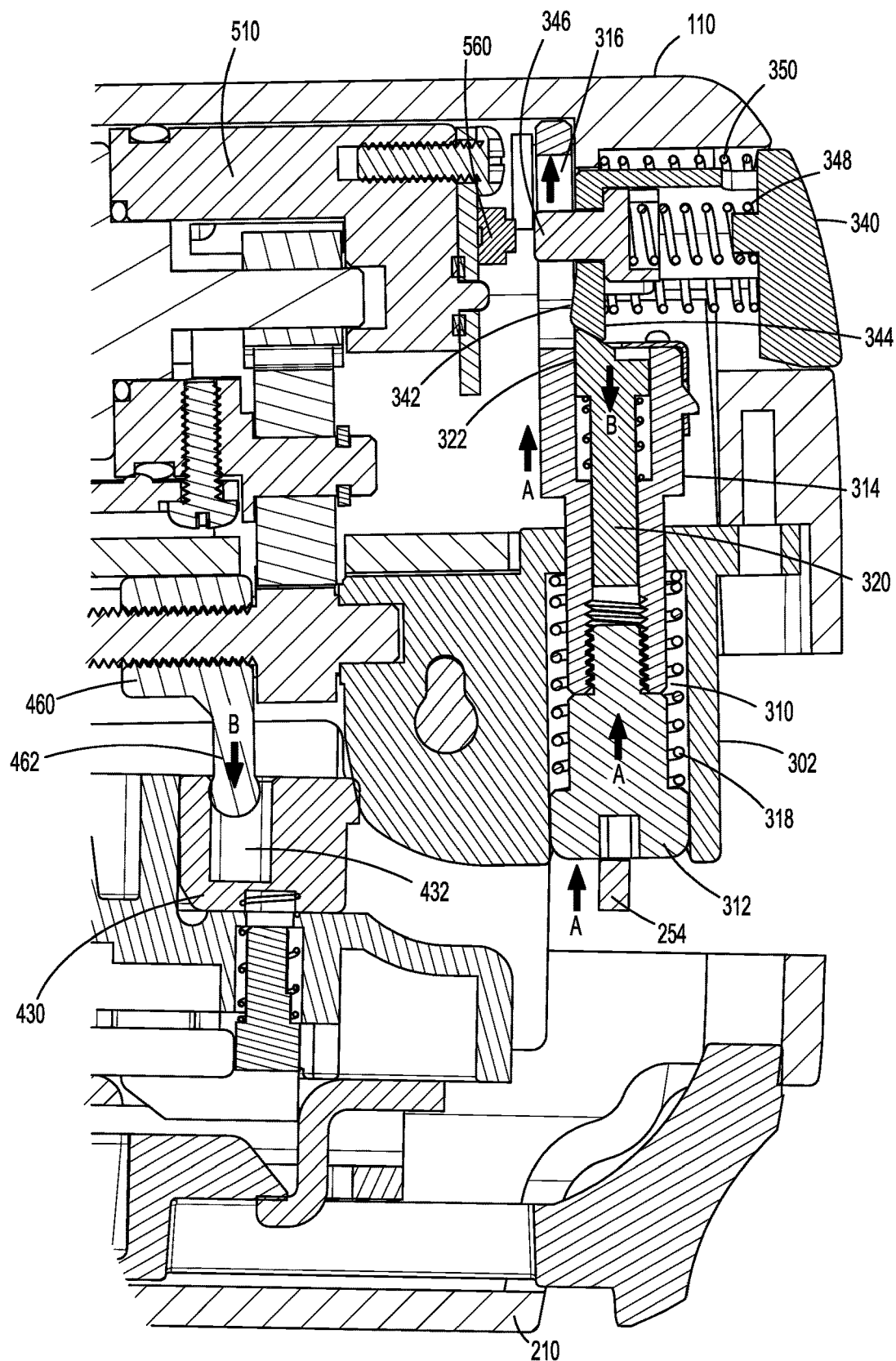
FIG. 12 is an enlarged view of the indicated area of detail shown in FIG. 11 illustrating the clamp detection assembly with the surgical stapling instrument in a clamped configuration.
Figure 14:
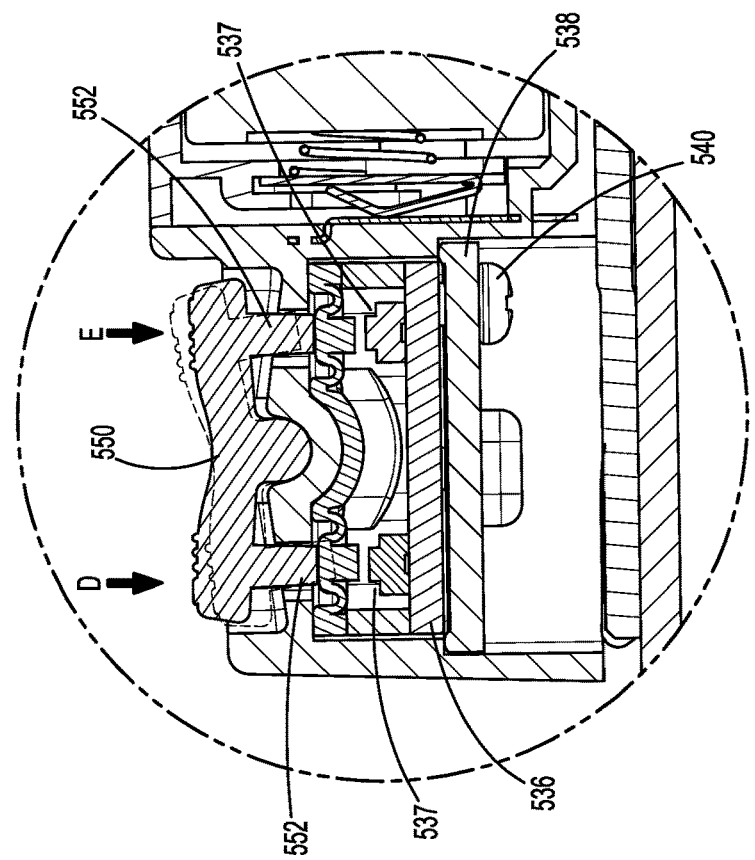
FIG. 14 is an enlarged view of the indicated area of detail shown in FIG. 11.
Figure 13:
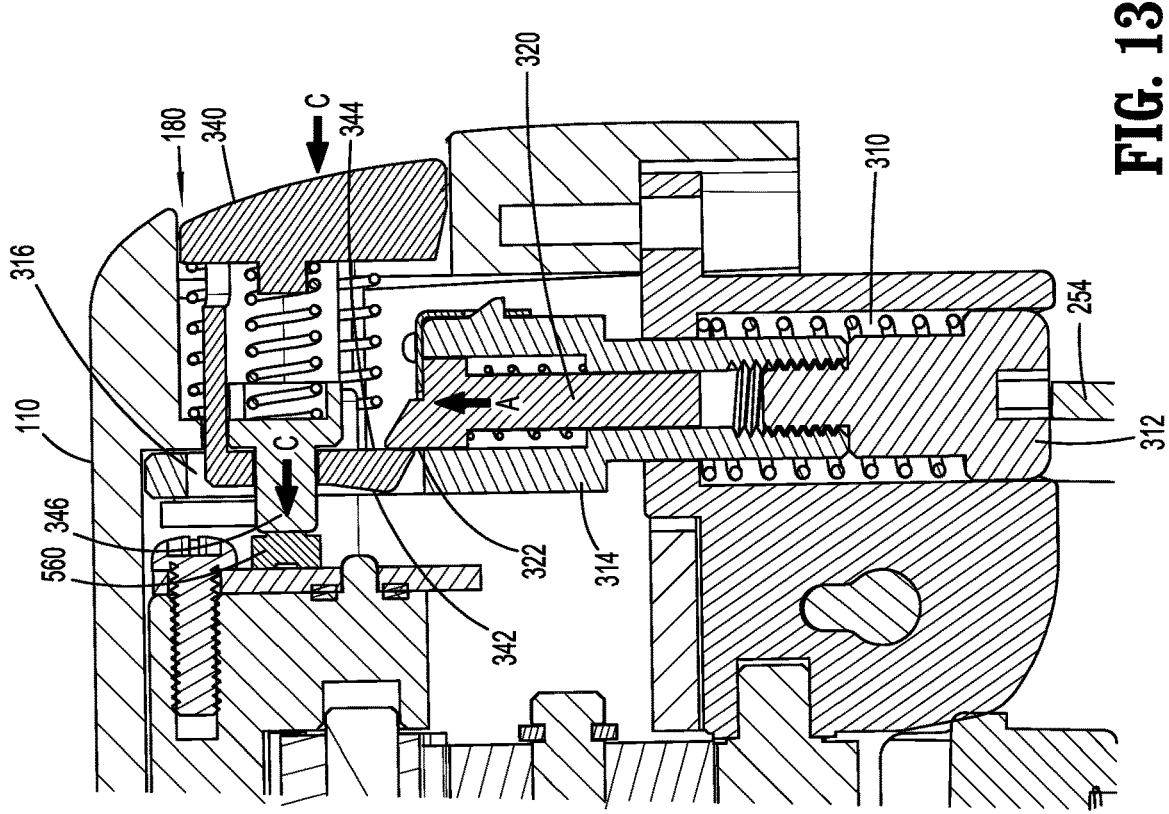
FIG. 13 is an enlarged view of a portion of the clamp detection assembly illustrating actuation of the safety button assembly.

Referring now to FIGS. 6, 7, and 9, the actuation switch 530 is illustrated in greater detail. The actuation switch 530 is positioned in the recess 160 of the first handle cover 110 and is actuated by a rocker 550 that is pivotable along the longitudinal axis "X-X" (FIG. 11). The recess 160 is located in a distal region of the first handle cover 110. The components of the actuation switch 530 are disposed on an under side of the recess 160. Specifically, a receptacle 532 sits adjacent the under side of the recess 160 and includes pushbuttons 533 that are aligned with posts 552 on an underside of the rocker 550. A pivot plate 534 rests against the receptacle 532 and a contact plate 536 is positioned adjacent the pivot plate 534. The contact plate 536 has switches 537 aligned with the pushbuttons 533 of the receptacle 532. A base plate 538 covers the contact plate 536 and fasteners 540 are used to secure the layers of the actuation switch 530 to the first handle cover 110. In a rest state, the rocker 550 is positioned such that the posts 552 do not engage the pushbuttons 533. With brief additional reference to FIG. 14, in a first actuated state, the rocker 550 is pivoted distally such that the distal post 552 moves in the direction indicated by arrow "D" and engages the corresponding pushbutton 533 and switch 537 to supply power to the motor 510 such that the motor 510 turns in a direction that rotates the drive gear 570 and the intermediate gear 580 to rotate the lead screw 410 and translate the slider 460 and actuation knob 430 distally. In a second actuated state, the rocker 550 is pivoted proximally such that the proximal post 552 moves in the direction indicated by arrow "E" and engages the corresponding pushbutton 533 and switch 537 to supply power to the motor 510 such that the motor 510 turns in an opposite direction that rotates the drive gear 570 to rotate the lead screw 410 and translate the slider 460 and actuation knob 430 proximally. Without user interaction, the rocker 550 returns to its rest state and the motor 510 is deenergized.

Figure 8:
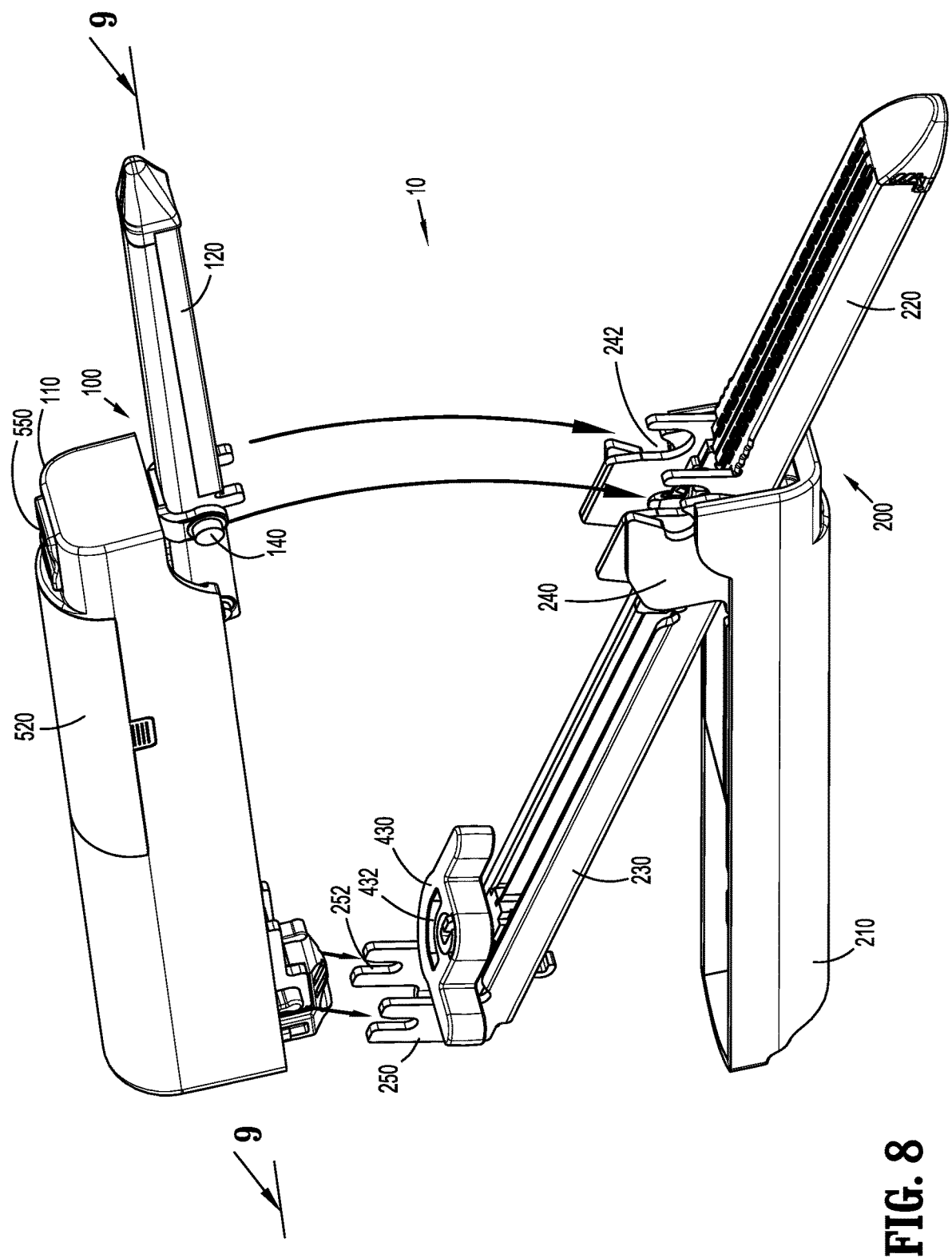
FIG. 8 is a perspective view of the surgical stapling instrument of FIG. 1 illustrating coupling an anvil portion with a cartridge portion.
Figure 15:
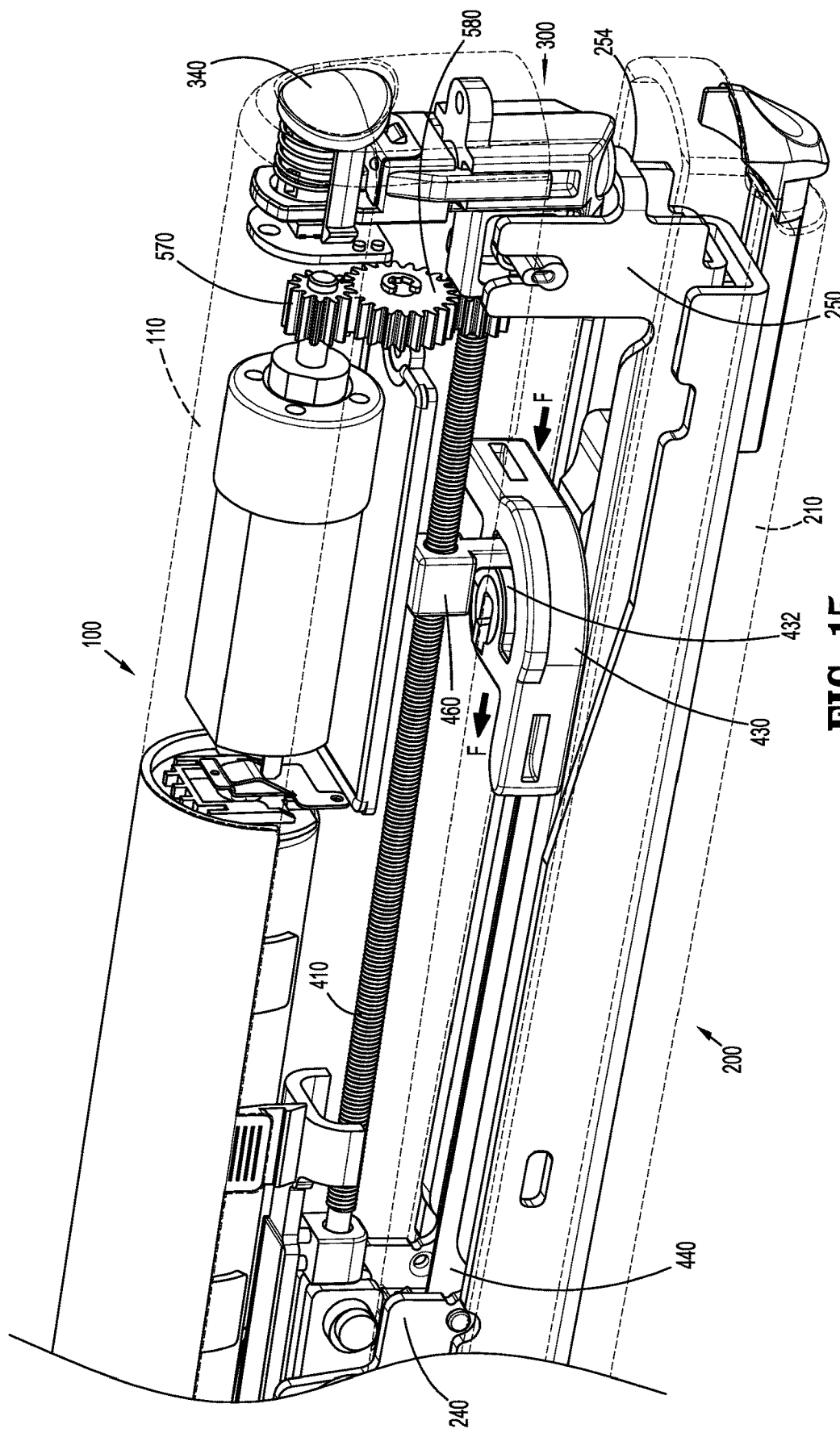
FIG. 15 is a perspective view of the handle assembly of FIG. 2 with both handle covers shown in phantom.

Operation of the surgical stapling instrument 10 and the clamp detection assembly 300 in particular will now be described with reference to FIGS. 8-13. Initially, as shown in FIGS. 8-10, the anvil portion 100 is separated from the cartridge portion 200 and is in the unclamped configuration. In the unclamped configuration, the first spring 318 urges the plunger 312 through the bottom opening in the housing 302. Translation of the plunger 312 in this direction is limited by engagement of the shoulder of the block 314 with the upper surface of the housing 302. The aperture 316 of the block 314 is out of alignment with the distal face 342 of the safety button 340 thereby inhibiting the safety button 340 from translating distally through the aperture 316. The projection 346 extends into the aperture 316 but remains spaced apart from the safety switch 560 and prevents the motor 510 from being energized by the actuation switch 530 as the safety switch 560 is in the disengaged position. Thus, in the unclamped configuration, the motor 510 cannot be operated. As shown in FIG. 11, the anvil portion 100 and the cartridge portion 200 are coupled together such that the first and second jaws 120, 220 are in close cooperative alignment and the anvil body 130 and the cartridge body 230 are juxtaposed. This arrangement defines the clamped configuration. In the clamped configuration, the anvil body 130 is pivoted towards the cartridge body 230 and the plunger engages a bridge 254 of a platform 250 on the cartridge body 230. In addition to the bridge, the platform 250 also includes notches 252 and each notch 252 is configured to receive a portion of the rod 380 therein (FIG. 15). When the plunger 312 engages the bridge 254 as the anvil and cartridge portions 100, 200 transition from the unclamped configuration to the clamped configuration, the plunger 312 travels away from the cartridge body 230, compresses the first spring 318, and moves the block 314 in the direction shown by arrows "A". This movement of the block 314 aligns the aperture 316 of the block 314 with the distal face 342 of the safety button 340. Additionally, the angled face 322 of the head of the safety pin 320 and angled surface 343 of the safety button 340 cammingly engage urging the safety pin 320 in the direction of arrow "B" and overcoming the bias of the second spring 330. Simultaneously, the finger 462 of the slider 460 also travels in the direction of arrow "B" and engages the cutout 432 of the actuation knob 430. In the clamped configuration shown in FIG. 12, the safety button 340 is now operable by a user to initiate operation of the surgical stapling instrument 10.

With the anvil and cartridge portions 100, 200 in the clamped configuration, the user is able to depress the safety button 340 at the proximal end of the first handle cover 110 and move the safety button 340 in the direction of arrows "C". As the aperture 316 of the block 314 is aligned with the distal face 342 of the safety button 340, the safety button 340 enters the aperture 316 and the projection 346 engages the safety switch 560 and transitions the safety switch 560 from the disengaged position to the engaged position. This enables the motor 510 to run in response to operation of the actuation switch 530. Further, the angled surface 343 of the safety button 340 slides distally beyond the angled face 324 of the head of the safety pin 320 which allows the safety pin 320 to move in the direction of arrow "A" such that a distal face 322 of the safety pin 320 engages an inner surface 344 of the distal face 342 of the safety button 340, which inhibits proximal movement of the safety button 340. Essentially, this secures the safety button 340 in a distal position which maintains the safety switch 560 in the engaged position without requiring constant pressure on the safety button 340 by the user. With additional reference to FIGS. 14 and 15, by positioning the safety switch 560 in the engaged position, the user may pivot the rocker 550 distally and actuate the actuation switch 530 thereby energizing the motor 510 to rotate the drive gear 570 in the first direction. The drive gear 570 engages the intermediate gear 580 which engages the gear 420 on the lead screw 410 and translates the slider 460 and actuation knob 430 distally as indicated by arrows "F". As the actuation knob 430 translates distally, the drive bar 440 also translates distally through the cartridge (i.e., advances). Pivoting the rocker 550 proximally energizes the motor 510 to rotate the drive gear 570 in the second direction that is opposite the first direction. This rotates the lead screw 410 in the opposite direction and translates the slider 460 and actuation knob 430 proximally (i.e., retracts).

While illustrated as being used in powered surgical stapling instrument 10, it is contemplated, and within the scope of the present disclosure for the surgical stapling instrument 10 to be configured for use with various electromechanical and/or electrosurgical instruments and systems. For example, the surgical stapling instrument 10 may be utilized in robotic surgical systems, such as the robotic surgical system shown and described in U.S. Pat. No. 8,828,023, the entire content of which is incorporated herein by reference.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:
    an anvil portion and a cartridge portion operably coupled thereto, the anvil and cartridge portions transitionable between clamped and unclamped configurations; and
    a clamp detection assembly including:
        a plunger slidably disposed in a chamber of a housing,
        a block attached to the plunger, the block having an aperture,
        a spring disposed in the chamber, the spring biasing the plunger and block towards the cartridge portion,
        a button slidably disposed in a recess of the anvil portion, the button including a distal face and a projection,
        wherein the spring urges the plunger and block towards an opening of the chamber and the aperture is out of alignment with the button in the unclamped configuration of the anvil and cartridge portions and engagement of the plunger with a bridge of the cartridge portion translates the plunger and the block away from the opening of the chamber such that the aperture is aligned with the button in the clamped configuration of the anvil and cartridge portions.

2. The surgical stapling instrument according to claim 1, further including a firing assembly having:
    an actuation knob translatable along a length of the cartridge portion,
    a lead screw, and
    a slider coupled to the lead screw such that rotation of the lead screw causes axial displacement of the slider, the slider configured to detachably engage the actuation knob to impart axial displacement to the actuation knob.

3. The surgical stapling instrument according to claim 2, further including an actuation assembly with:
    a motor operatively coupled to the lead screw,
    a battery pack electrically coupled to the motor to supply power thereto, and
    a first switch electrically coupled to the motor.

4. The surgical stapling instrument according to claim 3, wherein the distal face and the projection of the button are translatable through the aperture with the anvil and cartridge portions in the clamped configuration.

5. The surgical stapling instrument according to claim 4, wherein the projection is configured to engage a second switch of the actuation assembly, the second switch enabling activation of the motor.

6. The surgical stapling instrument according to claim 2, wherein the slider engages the actuation knob with the anvil and cartridge portions in the clamped configuration.

7. The surgical stapling instrument according to claim 3, wherein the battery pack is replaceable.

8. The surgical stapling instrument according to claim 3, wherein the first switch is transitionable between a first position that rotates the motor in a first direction causing rotation of the lead screw in the first direction and a second position that rotates the motor in a second, and opposite, direction causing rotation of the lead screw in the second direction.

9. A surgical stapling instrument comprising:
a cartridge portion configured to receive a loading unit;
an anvil portion operably coupled to the cartridge portion, the anvil and cartridge portions transitionable between clamped and unclamped configurations;
a firing assembly including:
an actuation knob translatable along a length of the cartridge portion,
a lead screw, and
a slider coupled to the lead screw such that rotation of the lead screw causes axial displacement of the slider, the slider configured to detachably engage the actuation knob to impart axial displacement to the actuation knob; and
an actuation assembly having:
a motor operatively coupled to the lead screw,
a battery pack electrically coupled to the motor to supply power thereto, and
a first switch electrically coupled to the motor, the first switch transitionable between a first position that rotates the motor in a first direction causing rotation of the lead screw in the first direction and a second position that rotates the motor in a second, and opposite, direction causing rotation of the lead screw in the second direction,
wherein actuation of a second switch on the anvil portion enables activation of the motor, the second switch actuatable when the anvil and cartridge portions are in the clamped configuration.

10. The surgical stapling instrument according to claim 9, wherein a button slidably disposed in a recess of the anvil portion is engageable with the second switch with the anvil and cartridge portions in the clamped configuration.

11. The surgical stapling instrument according to claim 10, further including a block with an aperture that is slidably disposed in the anvil portion, wherein the aperture is out of alignment with the button in the unclamped configuration of the anvil and cartridge portions and the aperture is aligned with the button in the clamped configuration of the anvil and cartridge portions.

12. The surgical stapling instrument according to claim 11, further including:
a plunger attached to the block and slidably disposed in a chamber of a housing, and
a spring biasing the plunger towards the cartridge portion, wherein the spring urges the plunger and block towards the cartridge portion and the aperture is out of alignment with the button in the unclamped configuration of the anvil and cartridge portions and engagement of the plunger with a bridge of the cartridge portion translates the block towards the anvil portion such that the aperture is aligned with the button in the clamped configuration of the anvil and cartridge portions.

13. The surgical stapling instrument according to claim 9, wherein the battery pack is replaceable.

14. The surgical stapling instrument according to claim 9, wherein the slider engages the actuation knob with the anvil and cartridge portions in the clamped configuration.

15. A surgical stapling instrument comprising:
an anvil portion and a cartridge portion operably coupled thereto, the anvil and cartridge portions transitionable between clamped and unclamped configurations;
a button slidably disposed in a recess of the anvil portion;
a block with an aperture that is slidably disposed in the anvil portion, the aperture out of alignment with the button in the unclamped configuration of the anvil and cartridge portions and the aperture is aligned with the button in the clamped configuration of the anvil and cartridge portions;
an actuation knob translatable along a length of the cartridge portion;
a lead screw; and
a slider coupled to the lead screw such that rotation of the lead screw causes axial displacement of the slider, the slider engaging the actuation knob to impart axial displacement to the actuation knob with the anvil and cartridge portions in the clamped configuration.

16. The surgical stapling instrument according to claim 15, further including:
a motor operatively coupled to the lead screw,
a battery pack electrically coupled to the motor to supply power thereto, and
a first switch electrically coupled to the motor and configured to select a direction of rotation of the motor,
wherein the button contacts a second switch on the anvil portion and enables activation of the motor with the anvil and cartridge portions in the clamped configuration.

17. The surgical stapling instrument according to claim 16, wherein the battery pack is replaceable.

18. The surgical stapling instrument according to claim 16, wherein the first switch is transitionable between a first position that rotates the motor in a first direction causing rotation of the lead screw in the first direction and a second position that rotates the motor in a second, and opposite, direction causing rotation of the lead screw in the second direction.

19. The surgical stapling instrument according to claim 15, further including:
a plunger attached to the block and slidably disposed in a chamber of a housing, and
a spring biasing the plunger towards the cartridge portion, wherein the spring urges the plunger and block towards the cartridge portion and the aperture is out of alignment with the button in the unclamped configuration of the anvil and cartridge portions and engagement of the plunger with a bridge of the cartridge portion translates the block towards the anvil portion such that the aperture is aligned with the button in the clamped configuration of the anvil and cartridge portions.

20. The surgical stapling instrument according to claim 15, wherein the slider is disengaged from the actuation knob with the anvil and cartridge portions in the unclamped configuration.

* * * * *